United States Patent
Tang et al.

(10) Patent No.: US 9,931,100 B2
(45) Date of Patent: Apr. 3, 2018

(54) METHOD AND DEVICE FOR LOCATING WIRELESS FETAL MONITORING PROBES IN SET AREA

(71) Applicant: Edan Instruments, Inc., Shenzhen, Guangdong Province (CN)

(72) Inventors: Lin Tang, Shenzhen (CN); Dewei Chen, Shenzhen (CN); Xin Yin, Shenzhen (CN)

(73) Assignee: Edan Instruments, Inc., Shenzhen, Guangdong (CN)

( * ) Notice: Subject to any disclaimer, the term of this patent is extended or adjusted under 35 U.S.C. 154(b) by 0 days.

(21) Appl. No.: 15/038,468

(22) PCT Filed: Apr. 15, 2015

(86) PCT No.: PCT/CN2015/076643
§ 371 (c)(1),
(2) Date: May 22, 2016

(87) PCT Pub. No.: WO2016/155038
PCT Pub. Date: Oct. 6, 2016

(65) Prior Publication Data
US 2017/0100090 A1 Apr. 13, 2017

(30) Foreign Application Priority Data
Mar. 31, 2015 (CN) .......................... 2015 1 0148525

(51) Int. Cl.
A61B 8/00 (2006.01)
G01S 5/02 (2010.01)
(Continued)

(52) U.S. Cl.
CPC .............. *A61B 8/00* (2013.01); *G01S 5/0252* (2013.01); *H04Q 9/00* (2013.01); *A61B 5/0002* (2013.01);
(Continued)

(58) Field of Classification Search
CPC ........ G01S 5/0009; G01S 5/02; G01S 5/0252; H04B 17/318; A61B 8/00; A61B 5/0002;
(Continued)

(56) References Cited

U.S. PATENT DOCUMENTS

| | | | | |
|---|---|---|---|---|
| 5,877,675 A * | 3/1999 | Rebstock | ............ | A61B 5/0002 128/903 |
| 6,560,442 B1 * | 5/2003 | Yost | ...................... | H04W 24/00 455/423 |

(Continued)

*Primary Examiner* — Hai Phan
*Assistant Examiner* — Franklin Balseca
(74) *Attorney, Agent, or Firm* — JCIPRNET

(57) ABSTRACT

The invention relates to a method and device for locating wireless fetal monitoring probes in a set area. The method comprises the following steps: instructions are sent via a plurality of wireless base stations to instruct the wireless probes in the action scopes of the wireless base stations to send base station signal intensity data tables; the wireless probes search all receivable base station signals, establish the base station signal intensity data tables; operations are carried out based on the received current base station signal intensity data tables and base station signal intensity data tables of reference points to obtain a distance reference table; the position of one with the smallest distance value is selected to be regarded as the current position of the corresponding probe. The method and the device have the benefits of quickly locating each wireless probe and avoiding loss of monitoring data.

11 Claims, 3 Drawing Sheets

(51) Int. Cl.
  *H04Q 9/00*      (2006.01)
  *A61B 5/00*      (2006.01)
  *H04B 17/318*    (2015.01)

(52) U.S. Cl.
  CPC .......... *A61B 5/0004* (2013.01); *A61B 5/0006* (2013.01); *A61B 5/0011* (2013.01); *A61B 5/0015* (2013.01); *H04B 17/318* (2015.01); *H04Q 2209/40* (2013.01)

(58) Field of Classification Search
  CPC ... A61B 5/0004; A61B 5/0006; A61B 5/0011; A61B 5/0015; H04Q 9/00; H04Q 2209/40
  See application file for complete search history.

(56) References Cited

U.S. PATENT DOCUMENTS

| | | | | |
|---|---|---|---|---|
| 2002/0013517 A1* | 1/2002 | West | ............ | A61B 5/1113 600/300 |
| 2006/0246922 A1* | 11/2006 | Gasbarro | ............ | A61B 5/0002 455/456.6 |
| 2008/0004538 A1* | 1/2008 | Virtanen | ............ | A61B 5/0006 600/509 |
| 2010/0328076 A1* | 12/2010 | Kyle | ............ | G06F 19/327 340/573.1 |
| 2011/0163916 A1* | 7/2011 | Bamidele | ............ | G01S 13/878 342/451 |
| 2014/0226503 A1* | 8/2014 | Cooper | ............ | H04W 4/043 370/252 |

\* cited by examiner

METHOD AND DEVICE FOR LOCATING WIRELESS FETAL MONITORING PROBES IN SET AREA

CROSS REFERENCE TO RELATED APPLICATIONS

The present application is the US national stage of International Patent Application PCT/CN2015/076643 filed on Apr. 15, 2015, which, in turn, claims priority to Chinese Patent Application CN201510148525.4 filed on Mar. 31, 2015.

TECHNICAL FIELD

The invention relates to medical equipment, in particular to a method and a device for locating wireless fetal monitoring probes in a set area.

BACKGROUND ART

A conventional fetal monitor and a central monitoring system composed of a plurality of the conventional fetal monitors both adopt wired probes, and each conventional fetal monitor comprises two fetal heart probes and a uterine contraction pressure probe. The connection cable of each wired probe is very long to avoid loss, but for one-to-one monitoring, one monitor is placed near each pregnant woman, the probes of the monitor are tied to the abdomen of the pregnant woman, and the three cables of the three probes are easy to twist together. Moreover, the pregnant woman cannot move freely, and the probes are required to be removed before the pregnant woman leaves the monitor, and need to be retied to the pregnant woman after the pregnant woman comes back, which is very inconvenient for use. Under the condition, each bed needs one fetal monitor in the prior art, and a plurality of fetal monitors may be arranged in one ward. Such deployment of the fetal monitors results in large number of fetal monitors, large area occupied by the fetal monitors, large electricity consumption of the fetal monitors, and difficulty of managing the data of the fetal monitors. In order to solve the problems occurred on the conventional medical wireless fetal monitoring probe, a multi-bed fetal monitor is adopted. The main principle of the multi-bed fetal monitor is that four or more groups of probes (each group of the probes comprises two fetal heart probes and one uterine contraction probe) are hung on one monitor body, a plurality of windows are displayed on one large-screen display, and each window corresponds to one pregnant woman, so that only one fetal monitor is arranged in a ward; moreover, the probes are wireless fetal monitoring probes, so that the system is concise, the occupied area is small, and the power consumption is smaller than the total power consumption of the fetal monitors arranged in one ward in the prior art. A doctor or nurse can observe the conditions of all pregnant women in one ward via the large-screen display, so that the work efficiency is improved; or, each bed can be equipped with one fetal monitor, and the fetal monitor is equipped with one group of probes (the group of the probes comprises two fetal heart probes and one uterine contraction probe), so that the cable consumption in one ward adopting the one-bed one-fetal monitor mode is reduced, and pregnant women in the ward can move freely after the probes are tied to the pregnant women. But the clinical use of wireless fetal monitoring probes in a hospital has several problems in the prior art. For example, as the wireless fetal monitoring probes are not "tied" to the fetal monitors via cables and the size of each probe is very small, the probes are easily lost and difficult to find. Moreover, as a pregnant woman can move freely after wireless fetal monitoring probes are tied to the pregnant woman, the position of the pregnant woman cannot be located fast when the doctor or nurse wants to find the pregnant woman. For example, when the doctor or nurse finds out the fetal heart rate of the pregnant woman is relatively low and the corresponding fetal monitor gives an alarm, and the doctor or nurse cannot examine the pregnant woman immediately while the pregnant woman is not in the ward. When the pregnant woman wearing the wireless fetal monitoring probes goes out of the range of a wireless pregnant network of the obstetrics and gynecology department in the hospital (e.g., taking a rest at a small garden of the hospital) without informing the doctor or nurse, the fetal heart data of the pregnant woman cannot be fed back promptly. Therefore, it cannot be known whether a probe gives an alarm or not. The doctor or nurse cannot find the pregnant woman easily, and the monitoring data and alarming events in the losing period cannot be known even the doctor or nurse finds the pregnant woman later.

SUMMARY

In order to solve the technical problems in the prior art, wireless fetal monitoring probes cannot be located, users are difficult to find and the data losing possibility is high, a method and a device, which are capable of locating the wireless fetal monitoring probes, facilitate user finding, avoid data loss, are provided and configured to locate the wireless fetal monitoring probes in a set area.

1. In order to solve the technical problems, a method for locating the wireless fetal monitoring probes in the set area is provided, comprising the following steps:
  A) a data management center sends instructions via a plurality of wireless base stations arranged at different positions in the set area to require the wireless fetal monitoring probes in the action scopes of the wireless base stations to send base station signal intensity data tables of received base station signals;
  B) each wireless fetal monitoring probe searches receivable signals of the base stations after receiving the instructions, quantizes the intensities of the received signals of the base stations, establishes a base station signal intensity data table in which signal intensities of the base stations are arranged according to the serial numbers of the base stations, and sends the base station signal intensity data table to the data management center via the base station of which the signal intensity is the largest; and
  C) operations based on each received current base station signal intensity data table sent by the corresponding wireless fetal monitoring probe and reference point base station signal intensity data tables which are obtained in advance and comprise base station signal intensities at a plurality of reference points in the set area are carried out to obtain a distance reference table; and the position of a reference point with the smallest distance value is selected to be regarded as the current position of the wireless fetal monitoring probe.

Furthermore, the method comprises the following steps before the step A:
  M) a plurality of wireless base stations are arranged at different positions in the set area; and
  N) the set area is divided into a plurality of locating sub-areas, and a reference point is arranged for each locating sub-area; the base station signal intensities at the reference points are acquired, and quantized to obtain the reference point base station signal intensity data tables; the reference point base station signal intensity data tables are saved.

Furthermore, the quantizing sub-step in the step B or step N comprises:

the receivable signal intensity value of each base station is regarded as the signal intensity value of the base station, while if no signal intensity value of a base station is receivable, zero is regarded as the signal intensity value of the base station; signal intensity values acquired by each wireless fetal monitoring probe or at a certain point are arranged according to the serial number sequence of the wireless base stations, so as to obtain the base station signal intensity data table or the reference point base station signal intensity data table of the point.

Furthermore, in a reference point base station signal intensity data table, the signal levels of all of the receivable signals of the base stations are required to be larger than a set signal level or signal intensity, otherwise, the requirement shall be met by moving a corresponding wireless base station(s) or increasing the number of the wireless base stations.

Furthermore, the method comprises the following steps:
D) the current positions of the wireless fetal monitoring probes are marked in a map drawn in advance.

Furthermore, the method comprises the following steps:
the data management center sends probe sounding instructions with identification numbers of the wireless fetal monitoring probes to enable buzzers on the wireless fetal monitoring probes matched with the identification numbers to sound after the wireless fetal monitoring probes receive the instructions;

Furthermore, the method comprises the following steps:
when a wireless fetal monitoring probe(s) cannot receive any signal of the wireless base stations, physiological data obtained by the wireless fetal monitoring probe(s), current state data of the wireless fetal monitoring probe(s) and time data are saved in the wireless fetal monitoring probe(s), and are sent to the data management center as long as the wireless fetal monitoring probe(s) can receive a signal(s) of the wireless base stations.

Furthermore, the data management center sends instructions to search the wireless fetal monitoring probes or exchange data with the wireless fetal monitoring probes via the wireless base stations connected with the data management center or wireless base stations of the data management center.

Furthermore, the method relates to a mobile terminal configured to download and display current position data of the wireless fetal monitoring probes from the data management center via the wireless base stations, enter a search mode when the mobile terminal finds wireless fetal monitoring probes disappear, emit electromagnetic waves the same as that of the wireless base stations, and display response information of the wireless fetal monitoring probes, so as to search the wireless fetal monitoring probes.

The invention further relates to a device for implementing the method, comprising:

a locating instruction sending unit configured to enable the data management center to send instructions via the wireless base stations arranged at different positions in the set area, so as to require the wireless fetal monitoring probes in the action scopes of the wireless base stations to send base station signal intensity data tables of received base station signals;

a base station signal intensity data table establishing unit configured to enable each wireless fetal monitoring probe to search receivable signals of the base stations after receiving the instructions, quantize the intensities of the received signals of the base stations, establish a base station signal intensity data table in which signal intensities of the base stations are arranged according to the serial numbers of the base stations, and send the base station signal intensity data table to the data management center via the base station of which the signal intensity is the largest; and a locating unit configured to carry out operations based on each received current base station signal intensity data table sent by the corresponding wireless fetal monitoring probe and the reference point base station signal intensity data tables which are obtained in advance and comprise the base station signal intensities at a plurality of reference points in the set area to obtain a distance reference table; and the position of a reference point with the smallest distance value is selected to be regarded as the current position of the wireless fetal monitoring probe.

The device further comprises:

a saving unit configured to save physiological data obtained by a wireless fetal monitoring probe(s), current state data of the wireless fetal monitoring probe(s) and time data in the wireless fetal monitoring probe(s) when the wireless fetal monitoring probe(s) cannot receive any signal of the wireless base stations, and send the saved data to the data management center as long as the wireless fetal monitoring probe(s) can receive a signal(s) of the wireless base stations; and a position marking unit configured to mark the current positions of the wireless fetal monitoring probes in a map drawn in advance.

Application of the method and the device, which are configured to locate the wireless fetal monitoring probes in the set area, has the following beneficial effects: as the wireless fetal monitoring probes detect the signal intensities, relative to the current positions of the wireless fetal monitoring probes, of the wireless base stations arranged at different positions, and compare the signal intensity values with signal intensity values acquired in advance by the wireless fetal monitoring probes at the reference points, so that the position of each wireless fetal monitoring probe can be located fast; moreover, when a wireless fetal monitoring probe(s) cannot receive a signal of the wireless base stations, physiological data acquired by the wireless fetal monitoring probe(s) and the state data of the wireless fetal monitoring probe(s) are saved, and sent to the data management center after the wireless fetal monitoring probe(s) is/are connected with the wireless base stations, that is, loss of monitoring data is avoided.

DETAILED DESCRIPTION

An embodiment of the invention is described in detail according to the drawings.

Figure 1:
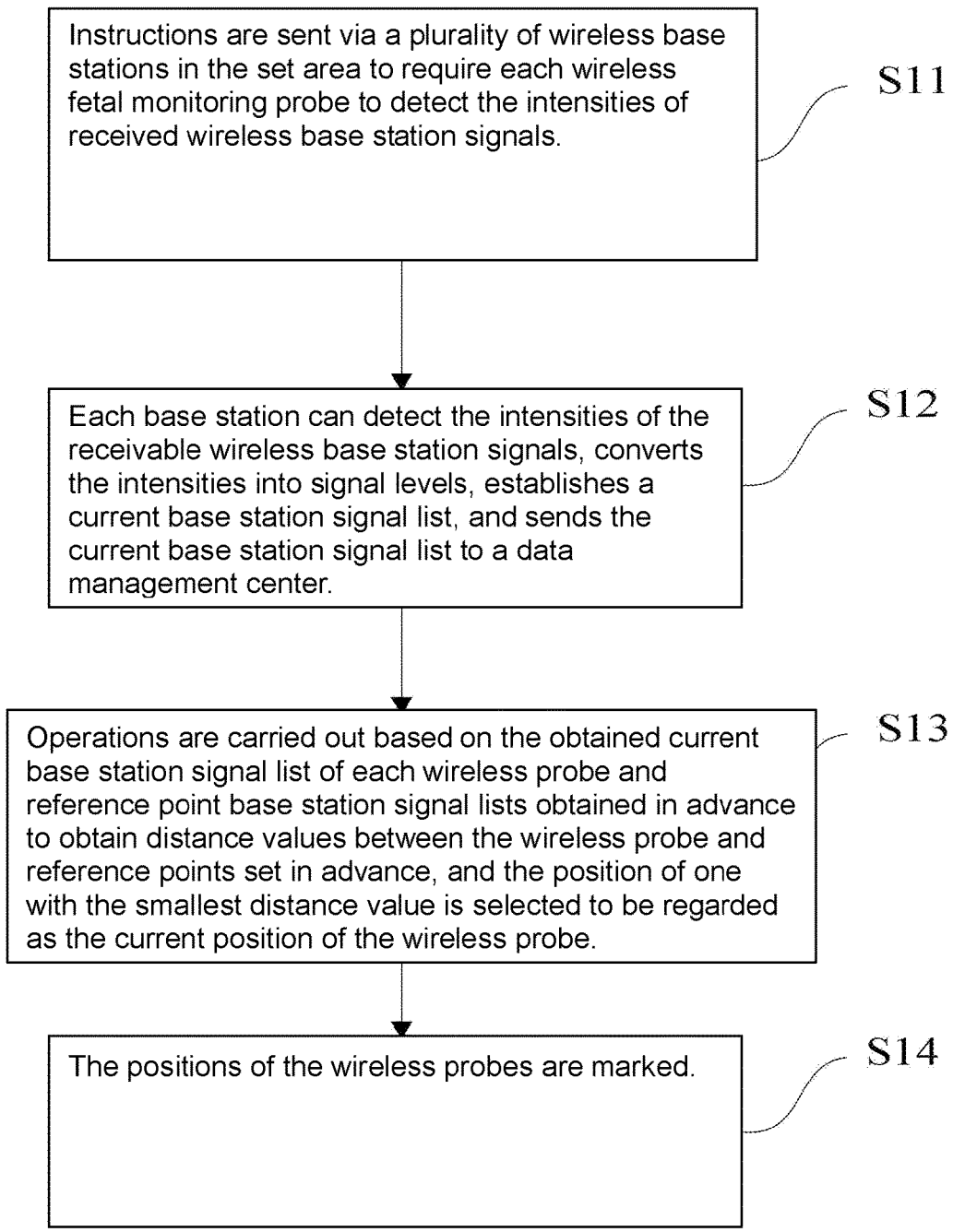
FIG. 1 is a flow diagram for locating wireless fetal monitoring probes in an embodiment of a method and a device which are configured to locate wireless fetal monitoring probes in a set area.

As shown in FIG. 1, in the embodiment of a method and a device, which are configured to locate wireless fetal monitoring probes in a set area, of the invention, the method configured to locate the wireless fetal monitoring probes in a set area, comprising step S11, step S12, step S13 and step S14.

In step S11, instructions instructing each wireless fetal monitoring probe to detect base station signal intensities received by the wireless fetal monitoring probe are sent in a set area via a plurality of wireless base stations, wherein according to the invention, a plurality of wireless fetal monitoring probes, the wireless base stations and at least one data management center are arranged in the set area (usually being an obstetric ward in a hospital or an accessory area of the obstetric ward), so as to form a monitoring network. In the monitoring network, all of the multiple wireless fetal monitoring probe are connected to the data management center via one or more of the wireless base stations, and the data management center receives, analyzes and saves physiological data, sent by the wireless fetal monitoring probe, of a user, so that fetal monitoring of the user and monitoring data saving are realized. Moreover, the data management center can send instructions via the wireless base stations, so as to instruct the wireless fetal monitoring probes in the action scopes of the wireless base stations to perform specified actions, such as sending special data and buzzing. Because the data management center is usually a computer installed with specialized software, a located wireless fetal monitoring probe(s) can be displayed on a map on the display screen of the computer, and a doctor or nurse can check the located wireless fetal monitoring probe(s). The ways of arranging the wireless base stations and dividing the set area are described in detail later. In the step S11, the data management center sends the instructions via the wireless base stations arranged at different positions in the set area to require the wireless fetal monitoring probes in the action scopes of the wireless base stations to send base station signal intensity data tables of received base station signals.

In step S12, each base station can detect the intensities of receivable signals of the wireless base stations, and converts the intensities into signal levels to establish a current base station signal list, and sends the current base station signal list to the data management center, wherein when receiving instructions sent by the wireless base stations, the wireless fetal monitoring probes in the action scopes of the wireless base stations respectively search all receivable base station signals (including signals sent by the wireless base stations), quantize the received base station signals to establish a base station signal intensity data table in which signal intensities of the base stations are arranged according to the serial numbers of the base stations, and send the base station signal intensity data tables to the data management center via the base station of which the signal intensity is the largest; and it's worth mentioning that each wireless fetal monitoring probe in the set area can send such a data table to the data management center. Specifically in the step S12, after receiving an instruction sent by a software base station, one wireless fetal monitoring probe searches all base stations of which signals are receivable, for example, if the number of the base stations, of which signals can be received by the wireless fetal monitoring probe, is i, the i base stations (APs) record practical signal intensity values r, the wireless base station signal intensity data table of the wireless fetal monitoring probe at current position is r=[rAP1, . . . , rAPm], and is sent to the data management center to the base station of which the signal intensity is the largest, wherein i is smaller than or equal to the total number of the wireless base stations, and r recorded by the m−i APs is 0.

In step S13, operations based on the current base station signal list of each wireless fetal monitoring probe and a reference point base station signal list obtained in advance are carried out to obtain distances between the wireless fetal monitoring probe and reference points set in advance, and the reference point which is nearest to the wireless fetal monitoring probe is selected to be regarded as the current position of the wireless fetal monitoring probe, wherein, the data management center processes each wireless base station signal intensity data table sent by the wireless fetal monitoring probes, and carries out operations based on the processed wireless base station signal intensity data table and the reference point base station signal intensity data table (saved in the data management center, and the acquiring or forming process of the reference point base station signal intensity data tables is explained later) of each reference point, so as to locate the wireless fetal monitoring probe. Specifically, during locating of a wireless fetal monitoring probe, operations based on a received current base station signal intensity data table sent by the wireless fetal monitoring probe and the reference point base station signal intensity data tables which are obtained in advance and comprise base station signal intensities at a plurality of reference points in the set area are carried out to obtain a distance reference table; and the position of a reference point with the smallest distance value is selected to be regarded as the current position of the wireless fetal monitoring probe. In the step S13, the distances between the position of each probe and the base stations are obtained by processing the base station signal intensities received by the wireless fetal monitoring probe and reference base station signal intensities according to various methods such as the weighed distance reversal method, the Kriging method or the Euclidean distance method, that is, establish a base station layout and a detection scope map database. Wherein, the compared with the other two methods, the Euclidean distance method is relatively simple to implement; moreover, as being implemented in a special area in a hospital, a database cannot be too large; the other two methods has various empirical parameters and interpolating calculation, so that the Euclidean distance method is higher in precision than the other two methods. Therefore, distance acquisition or database establishing is explained according to the Euclidean distance method in the embodiment. Operations based on the current wireless base station signal intensity data table sent by one wireless fetal monitoring probe and a reference point signal intensity database are carried out according to the formula:

$$Ei = \sqrt{\sum_{j=1}^{m} (r_{AP_j} - R_{AP_j})^2}, i \in (1, n)$$

so as to obtain a distance reference table, wherein m is the total number of the wireless base stations in the set area, i is the number of the base stations of which signals can be received by the wireless fetal monitoring probe, rAP is the signal intensity of the j-th wireless base station of the signal intensity data table sent by the wireless fetal monitoring probe; the operations based on one current wireless base station signal intensity list of the wireless fetal monitoring probe and the reference point signal intensity lists of i reference points are carried out, so as to obtain i distance values, and establish the current distance reference list of the wireless fetal monitoring probe, and the smallest distance value is selected to be regarded as the current position of the probe. The positions of all of the wireless fetal monitoring probes in the set area (or the action scopes of all of the wireless base stations) can be obtained separately by conducting the processing on all wireless fetal monitoring probes sending wireless base station signal intensity data tables to the data management center separately.

In step S14, the positions of the wireless fetal monitoring probes are marked, wherein, the positions of the wireless fetal monitoring probes are marked on a map in which the set area is marked, wherein the source of the map is explained in further detail later.

Figure 2:
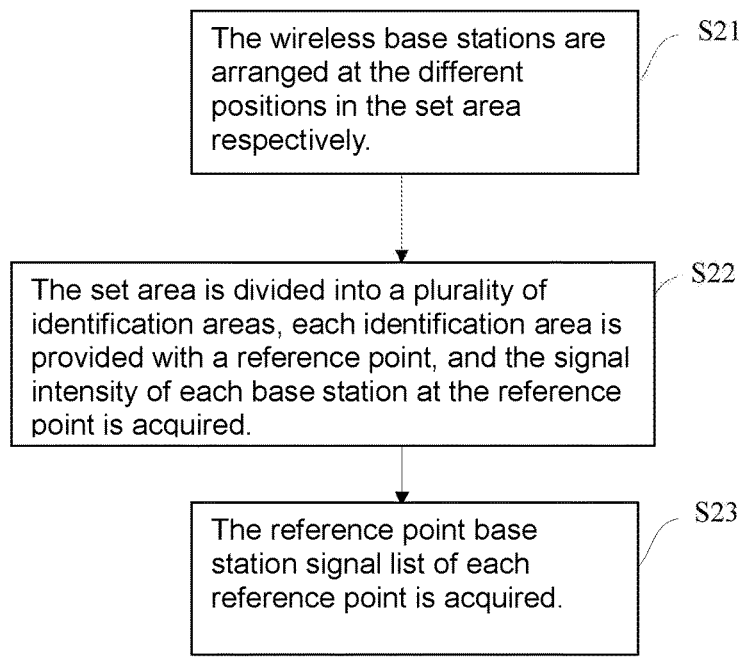
FIG. 2 is a flow diagram for establishing a reference point base station signal intensity data list in an embodiment of the invention.

According to the invention, the wireless base stations are required to be arranged in the set area before executing the steps, wherein signals of the wireless base stations can cover all positions in the set area, so that only if a user of the wireless fetal monitoring probes is in the set area, the wireless fetal monitoring probes worn by the user can connected with at least one of the wireless base stations, and send acquired physiological data to the data management center via the wireless base stations, and also can receive an instruction, sent by the wireless base stations, of the data management center. As in reality, the shape of set areas in hospitals are different, the positions and the numbers of wireless base stations arranged in the set areas are different, instead of being fixed. But wireless base station arranging and set area dividing are regular. Specifically, the wireless base station arranging step in each set area comprises steps S21, S22 and S23 shown in FIG. 2.

In step S21, a plurality of wireless base stations are arranged at different positions in the set area respectively, wherein, the wireless base stations are respectively arranged at different positions in the set area, and the positions of the wireless base stations meet the requirement that signals of the wireless base stations cover the set area and are kept in a certain signal intensity. It's worth mentioning that no boundary exists between the step S21 and the step S22, wherein the step S22 can be carried out after the step S21 in many cases, while if conditions or acquired data cannot confirm to requirements, the step S21 is carried out for two or more times till the acquired data is relatively satisfactory, and then the step S22 is carried out. But, once being arranged, the wireless base stations are not changed any more in at least a locating or monitoring process for a certain time. It's worth mentioning that in the reference point base station signal intensity data tables of all of the reference points, the signal levels of all of the receivable signals of the base stations are required to be larger than a set signal level or signal intensity, otherwise, the requirement shall be met by moving a corresponding wireless base station(s) or increasing the number of the wireless base stations.

In step S22, the set area is divided into a plurality of identification areas, a reference point is arranged in each identification area, and the signal intensity of each base station at the reference point is acquired, wherein the set area is divided into a plurality of locating sub-areas, one reference point is arranged for each locating sub-area, and base station signal intensities of the reference points are obtained.

In step S23, the reference point base station signal list of each reference point is acquired, wherein reference point base station signal intensity data tables of the reference points are acquired in sequence and saved separately.

Specifically, according to the invention, the step of arranging the wireless base stations and the step of dividing the set area into location areas do not have strict order, and all that is needed is that a reference point base station signal intensity data table meeting requirements can be obtained. For example, a "base station layout and detection scope map" of a wireless fetal monitoring probe network can be drawn according to the layout of a hospital, wherein the drawing comprises the following steps: first, obtaining an architectural plan of a floor, where the network is to be mounted, of the hospital to master each department and the layout of the hospital, simplifying the architectural plan with a drawing tool, and inputting the simplified plan into software to obtain the "base station layout and detection scope map" in which the distribution of the layer (namely, the set area) can be seen visually; arranging the base stations according to the floor structure of the set area, and recording mAP (AP1 to APm); detecting the signal intensities R of the base stations via the wireless fetal monitoring probes, for example R comprises 9 levels, wherein level 1 is the lowest level; detecting the signal intensities of the base stations via the wireless fetal monitoring probes in the base station arranging process, and dividing the signal intensities into the 9 levels, wherein the signal intensity is required to be not lower than level 3 to ensure smooth communication, so that if the signal intensity of any position where the wireless fetal monitoring probes may be used is too weak, one base station or mobile base station is added till the number of all base stations is m to ensure that the signal intensity of each wireless fetal monitoring probe at any use point is larger than or equal to level 3; dividing the simplified plan into N "identification areas" according to such a method that each identification area is 1.5 $m^{<2>}$, and marking the identification areas with 1 to n; marking any point, usually the central point, of the area i (1 to n) as Si (S1 to Sn); putting a wireless fetal monitoring probe at the selected Si, scanning the signal intensity R of surrounding AP(s) via the probe, and transmitting obtained data to a computing and processing unit, saving the obtained data, and recording a signal intensity data table $RSi=[RAP1, RAPm]$, wherein among the obtained data, the number of base stations sending signals is I which is smaller than or equal to m, the I base stations (APs) record practical R values, and the R value of m−I AP(s) is zero, that is, the practically detected signal intensity R is recorded by the I AP(s), the other m−I AP(s) do(es) not send signals, the signal intensity of the other m−I AP(s) is recorded as zero, and the records are summarized into the signal intensity data table $RSi=[RAP1, \ldots, RAPm]$ of the reference point; and circularly detecting and saving the R tables of all of the reference points (S1 to Sn) to obtain the reference point signal intensity data tables of the reference points. Each reference point is processed according to the above steps to obtain the reference point signal intensity data tables of all of the reference points; and the reference point signal intensity data tables are saved in the data management center.

According to the invention, if a signal of one base station is acquired by a wireless fetal monitoring probe, the signal is expressed by the received intensity of the signal; if a signal of one base station cannot be acquired by a wireless fetal monitoring probe, the signal is expressed as zero; signal levels of a certain point are arranged according to the serial number sequence of the wireless base stations, so as to obtain the signal intensity data table or a reference point signal intensity data table of the point. For identification of signals of the base stations, the problem that a signal of a base station cannot be identified is solved because all of the signals sent by the base stations carry identification codes of the corresponding base stations. The identification codes exist on the wireless base stations before the wireless base stations leave factory, for example, the identification codes are equivalent to hardware identification codes of hardware addresses of a network. Likewise, identification codes, similar to the identification codes on the wireless base stations, also exist on the wireless fetal monitoring probes, and any signal sent by the wireless fetal monitoring probes carries a corresponding identification code, so that the data management center or the wireless base stations can identify the source of the signal.

Figure 3:
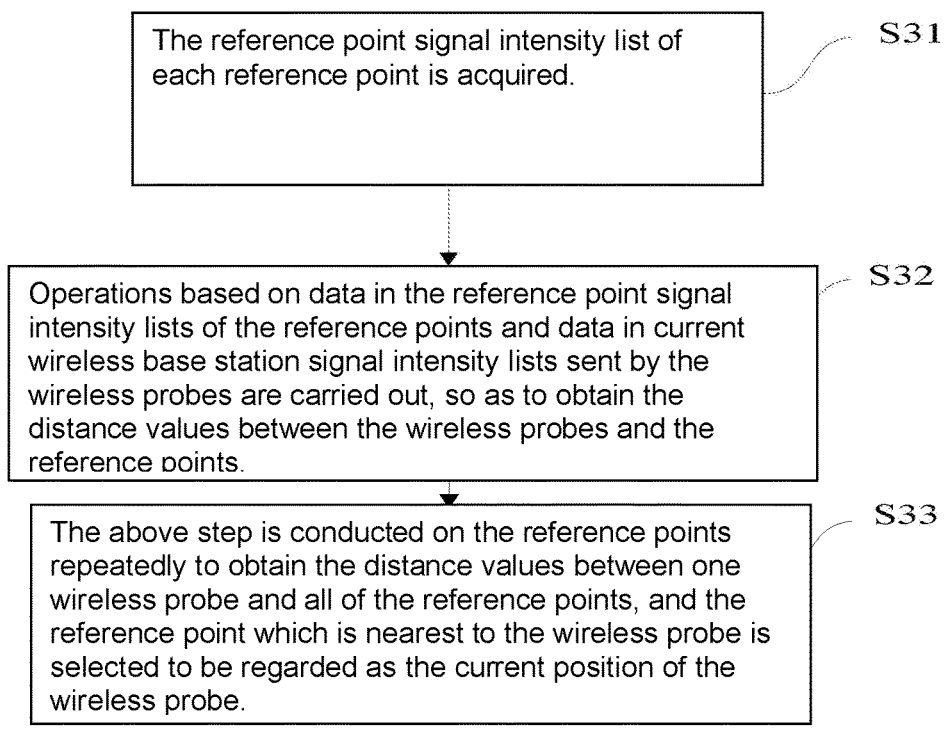
FIG. 3 is a flow diagram for establishing a wireless fetal monitoring probe distance list in an embodiment of the invention.

According to the invention, the data management center will process a plurality of signal intensity data tables sent by the wireless fetal monitoring probes, so as to locate each wireless fetal monitoring probe. The data management center performs the processing step, as many times as the wireless fetal monitoring probes send signal intensity data tables For one wireless fetal monitoring probe, the special processing or operation process is shown in FIG. 3, and comprises steps S31, S32 and S33.

In step S31, a reference point signal intensity list of one reference point is obtained, wherein, the obtained reference point signal intensity list of the reference point is detected in advance as mentioned.

In step S32, operations based on data in the reference point signal intensity lists of the reference points and data in current wireless base station signal intensity lists sent by the wireless fetal monitoring probes are carried out according to a formula, so as to obtain the distance values between the wireless probes and the reference points, wherein, the distance parameter between each probe and a reference point can be obtained by conducting operations on the reference point signal intensity list of the reference point and a current wireless base station signal intensity list sent by the wireless fetal monitoring probe according to the formula $$Ei = \sqrt{\sum_{j=1}^{m} (r_{AP_j} - R_{AP_j})^2}, i \in (1, n).$$

In step S33, the above step is conducted on all of the reference points to obtain the distance values between the wireless fetal monitoring probe and all of the reference points, and the reference point which is nearest to the wireless probe is selected to be regarded as the current position of the wireless fetal monitoring probe, wherein the distance between the probe and one wireless base station is obtained according to the step S31 and the step S32, while according to the invention, the number of the reference points is n, so that the step S31 and the step S32 are repeated n times to obtain the reference point base station signal intensity data tables including all of the reference points, n distance values are obtained, and the reference point of which the distance value is smallest (that is, the reference point of an identification area is nearest to the wireless fetal monitoring probe) is selected to be regarded as the current position of the wireless fetal monitoring probe.

It's worth mentioning that the repeating times of the steps (S31 to S32) depend on the number of the wireless base station signal intensity lists received by the data management center and sent by the wireless fetal monitoring probes, so as to locate the wireless fetal monitoring probes separately.

Moreover, as a wireless fetal monitoring probe(s) leaving the set area cannot be connected the base stations, monitoring data of the wireless fetal monitoring probe(s) cannot be transmitted to the data management center for processing and saving. In order to receive the data, physiological data obtained by a wireless fetal monitoring probe(s) which cannot receive any signal of the wireless base stations, current state data of the wireless fetal monitoring probe(s) and time data are saved in the wireless fetal monitoring probe(s) and are sent to the data management center as long as the wireless fetal monitoring probe(s) can receive a signal(s) of the wireless base stations.

According to the invention, the data management center sends instructions to search the wireless fetal monitoring probes or exchange data with the wireless fetal monitoring probes via the wireless base stations connected with the data management center or wireless base stations of the data management center. That is to say, besides the data management center, the wireless base stations and the wireless fetal monitoring probes, the device can further comprise a mobile terminal which can be connected with the system via any wireless base station to download reference point base station signal intensity lists, a map and identification area dividing data and the like from the data management center, or the current position information, identified or confirmed by the data management center, of the wireless fetal monitoring probes from the data management center. In a sense, the mobile terminal can be regarded as a simplified mobile data management center. According to the invention, the mobile terminal is mobile computer equipment which can be carried about by operation staff, and movable, can send wireless base station signals, and can be connected with the wireless base stations, such as a notebook computer or an IPAD.

Figure 4:
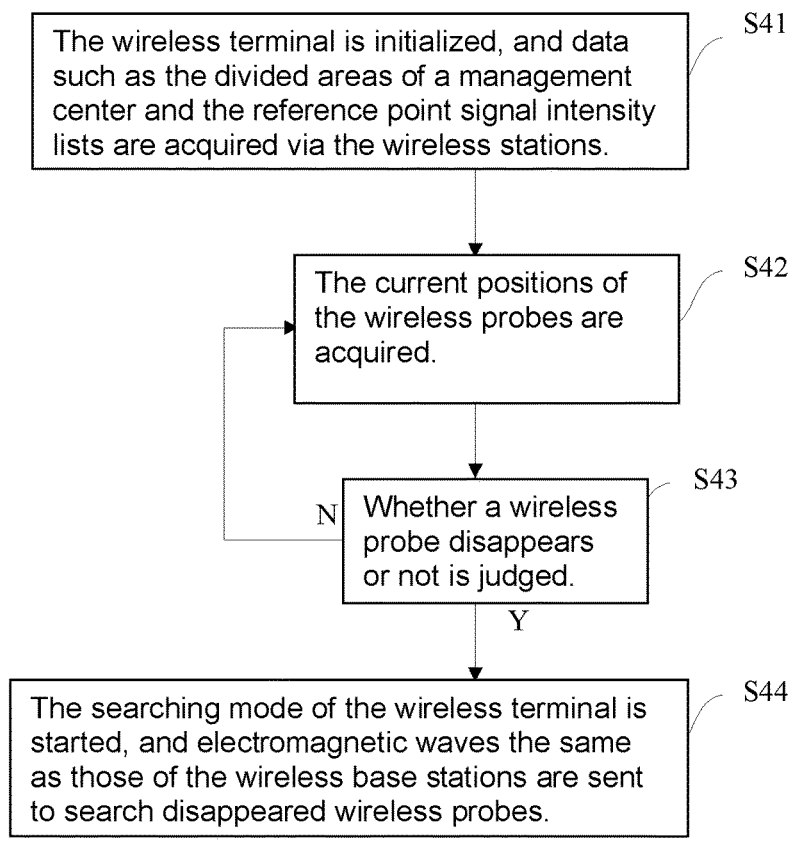
FIG. 4 is a flow diagram for searching a wireless fetal monitoring probe via wireless base stations in an embodiment of the invention.

The work flow and the method flow of the mobile terminal are shown in FIG. 4. In FIG. 4, the work flow and the method flow of the mobile terminal comprise steps S41, S42, S43 and S44.

In step S41, the mobile terminal is initialized, data about area dividing of the data management center, reference point signal intensity lists and the like are obtained via the wireless base stations, wherein, reference point signal intensity list, data required by work of the mobile terminal is obtained from the data management center; the wireless terminal is initialized to search a wireless network emitted by the base stations; software is initialized after the wireless terminal is started, so as to find a base station signal(s), be connected to the corresponding base station(s) if the base station signal(s) exist(s), and accessed into the wireless network, and communicate with the computing and processing unit(s) of the base station(s); the mobile terminal is connected with a networked to download and update data of a "base station layout and detection scope map" of the data management center, for example, the data can be updated once a minute.

In step S42, the current positions of the wireless fetal monitoring probes are acquired, wherein, all position information of the wireless fetal monitoring probes is downloaded from the data management center, and saved in the MCU of the mobile terminal; moreover, all alarming event information is downloaded from the data management center, and saved in the MCU of the mobile terminal; if an alarming signal exists, the mobile terminal drives the buzzer of the mobile terminal to sound, and the alarming information is displayed when required; in the same way, the "base station layout and detection scope map" can be displayed on the mobile terminal, and the positions of the wireless fetal monitoring probes and alarming symbols are marked on the "base station layout and detection scope map".

In step S43, whether a wireless fetal monitoring probe disappears or not is detected, wherein step S44 is carried out if the wireless fetal monitoring probe disappears, otherwise, the step S43 is repeated.

In step S44, a searching mode of the wireless terminal is started to send electromagnetic waves the same as those of the wireless base stations and search disappeared wireless fetal monitoring probes, wherein, the mobile terminal enters the searching mode to send the electromagnetic waves, so that the disappeared wireless fetal monitoring probes are searched by the mobile terminal carried about by a doctor or nurse.

According to the invention, the mobile terminal is configured to search an existing wireless fetal monitoring probe which moves out of the set area, so as to acquire the monitoring data generated in the state, losing connection with the wireless base stations, of the wireless fetal monitoring probe, and upload the data to the data management center and the like. In other words, the wireless terminal, as an important part of the system, is mainly carried about by the doctor or nurse. That is to say, the mobile terminal is a mobile simplified "computing and processing unit" in a wireless network as long as the wireless network is composed of base stations, and configured to alarm, display and the like, wherein the positions of the wireless fetal monitoring probes and related alarming events can be looked over from the mobile terminal. Other important functions of the mobile terminal and the data management center is to record and save the motion trails of a pregnant woman, and track and search the pregnant woman. Therefore, the data management center and the mobile terminal both detect the position information of the wireless fetal monitoring probes in real time, and record the information in chronological order to form the motion trails of the wireless fetal monitoring probes.

When existing wireless fetal monitoring probes disappeared (usually caused by the fact that the user of the existing wireless fetal monitoring probe moves out of the set area), the looking over and searching function of the mobile terminal is started; when both the base stations and the wireless terminal cannot detect the position information of the wireless fetal monitoring probes, the looking over and searching function of the mobile terminal is started automatically, an RF module in the mobile terminal is controlled to send signals the same as those of the base stations under the action of the mobile terminal, and search the wireless fetal monitoring probes according to saved information of the wireless fetal monitoring probes, so that the mobile terminal becomes a mobile "base station" configured to search the wireless fetal monitoring probes, establish wireless connection and communication, and search the wireless fetal monitoring probes finally. At the moment, the mobile terminal sends instructions requiring connection constantly as a mobile base station, so that when the doctor or nurse carrying about the mobile terminal searches the disappeared wireless fetal monitoring probes in the hospital, and moves to a position which is a certain distance away from the disappeared wireless fetal monitoring probes t (tied to the pregnant woman), the wireless fetal monitoring probes can be identified as long as appearing in the scope of the signal circle (namely the action scope of the mobile terminal) of the mobile terminal, the signal intensities, displayed in the screen of the mobile terminal, of the wireless fetal monitoring probes are relatively weak and shown at the edge of the "circle", and the mobile terminal exerts groups of 8 kHz pulses on buzzers of the wireless fetal monitoring probes at 3 s intervals to enable the buzzers to sound. If the doctor or nurse carrying about the mobile terminal moves in a direction away from the wireless fetal monitoring probes, the signals of the wireless fetal monitoring probe become weaker and disappear, the "circle" disappears from the display, and the buzzers stop sounding. At the moment, the doctor or nurse is required to move in a reverse direction, the signals of the wireless fetal monitoring probe become stronger gradually, the signal intensities, displayed in the screen of the mobile terminal, of the wireless fetal monitoring probes become stronger and are shown at the edge of the "circle", the radius of the "circle" becomes smaller, and a buzzer of the mobile terminal sends groups of 8 kHz pulses at 2 s intervals instead of 3 s intervals, that is to say, the mobile terminal gradually reduces the radius of the "circle" according to the signal intensities of the wireless fetal monitoring probes, the intervals of the groups of pulses are shortened, and when the probes are found, the "circle" is replaced by a "point", and the buzzer of the mobile terminal sends sound with no interval.

After the doctor or nurse finds the pregnant woman, the mobile terminal downloads all data from the wireless fetal monitoring probes, the wireless fetal monitoring probes taking the mobile terminal as a base station transmit data, and cancel wireless signal loss alarms; after the doctor or nurse returns to the covering scope of the wireless network, the wireless fetal monitoring probes communicate with the wireless terminal and the base stations, data of the wireless fetal monitoring probes are sent to the data management center via the base stations, that is to say, the data management center cancels "wireless signal loss alarms of the wireless fetal monitoring probes" and download history data from the mobile terminal.

The wireless terminal sends the saved wireless fetal monitoring probe data to the computing and processing unit, the computing and processing unit cancels "wireless signal loss alarms of the wireless fetal monitoring probes", and connects the data with data in a pregnant database according to a time scale to avoid loss of the data.

Moreover, the data management center also can be configured to better manage unused wireless fetal monitoring probes, for example, perform the function of making a vacant wireless fetal monitoring probe to alarm, so as to inform the doctor or nurse to charge the mobile probe in time, and further avoid the phenomenon that electricity in the mobile probe is used up. Specifically, the data management unit searches all wireless fetal monitoring probes in real time, and detects the states of the wireless fetal monitoring probes to find out whether the states of the wireless fetal monitoring probes are non-charging state or not; moreover, when two monitoring signals sent by the wireless fetal monitoring probes cannot be detected, for example, if the state that the wireless ultrasonic probes cannot detect a fetal heart rate and the uterine contraction pressure cannot detect uterine contraction pressure lasts for 10 minutes, the wireless fetal monitoring probes are vacant and unused; the data management center display the positions of all of the vacant wireless fetal monitoring probes and marks the positions in red to alert the user to place the vacant wireless fetal monitoring probes back onto charging seats; meanwhile, the buzzers of the unused wireless fetal monitoring probes can sound to alert the doctor or nurse to treat the wireless fetal monitoring probes.

Figure 5:
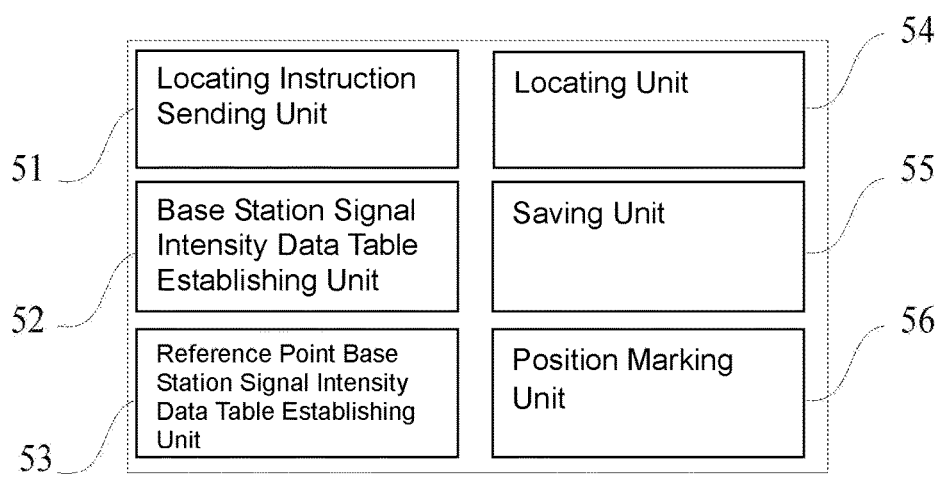
FIG. 5 is a structure diagram of the device in an embodiment of the invention.

As shown in FIG. 5, the invention further relates to a device for implementing the method, the device comprising a locating instruction sending unit 51, a base station signal intensity data table establishing unit 52, a locating unit 54, a reference point base station signal intensity data table establishing unit 53, a saving unit 55 and a position marking unit 56. Wherein the locating instruction sending unit 51 is configured to mark the data management center to send instructions via the wireless base stations arranged at different positions in the set area, and require the wireless fetal monitoring probes in the action scopes of the wireless base stations to send received base station signal intensity data tables; the base station signal intensity data table establishing unit 52 is configured to search receivable base station signals, quantize the received base station data, establish base station signal intensity data tables according to the serial numbers of the base stations, and send a received signal of which the intensity is the largest to the data management center; the locating unit 54 is configured to carry out operations based on a current base station signal intensity data table sent by a wireless fetal monitoring probe and reference point base station signal intensity data tables which are obtained in advance and comprise base station signal intensities of a plurality of reference points in the set area, so as to obtain a distance reference table between the current position of the wireless fetal monitoring probe and the reference points, wherein the reference point with the smallest distance value is selected to be regarded as the current position of the wireless fetal monitoring probe; the reference point base station signal intensity data table establishing unit 53 is configured to divide the set area into a plurality of locating sub-areas, each of which comprises a reference point, acquire the base station signal intensities at each reference point, quantize base station signal intensities, and establish and save a reference point base station signal intensity data table; the saving unit 55 is configured to save acquired physiological data of a wireless fetal monitoring probe which cannot receive any signal of the wireless base stations, the current state data of the wireless fetal monitoring probe, and time data into the wireless fetal monitoring probe, and send the saved data to the data management center when the wireless fetal monitoring probe can receive a signal(s) of the wireless base stations; and the position marking unit 56 is configured to mark the current positions of all of the wireless fetal monitoring probes on a map which is drawn in advance.

Furthermore, the locating unit 54 further comprises a distance reference table establishing module (not shown in FIG. 5) which is configured to carry out the following calculation:

$$Ei = \sqrt{\sum_{j=1}^{m} (r_{AP_j} - R_{AP_j})^2}, i \in (1, n)$$

so as to obtain the distance reference table, wherein m is the total number of the wireless base stations in the set area, i is the number of the reference points, rAP is the signal intensity level of the j-th wireless base station in the signal intensity data table sent by one wireless fetal monitoring probe; the operations based on one current wireless base station signal intensity list of the wireless fetal monitoring probe and the reference point signal intensity lists of i reference points are carried out, so as to obtain i distance values, and establish a distance reference list. It's worth mentioning that according to the invention, operations executed by the distance reference table establishing module may be different when different computing methods are adopted, but the distance same reference lists can be obtained finally.

The above embodiments only express several implementation methods of the invention specifically in detail. However, the patent scope of the invention is not limited to this. It should be noted that any transformation or improvement, which is based on the concept of the invention, capable of being thought by a common technician with skill in the art of the invention shall fall into the protection scope of the invention. Therefore, the protection scope of the invention should be subject to the attached claims.

What is claimed is:

1. A method for locating wireless fetal monitoring probes in a set area, comprising the following steps:
    A) a data management center sends instructions via a plurality of wireless base stations arranged at different positions in the set area to instruct the wireless fetal monitoring probes in the action scopes of the wireless base stations to send base station signal intensity data tables of received base station signals;
    B) the wireless fetal monitoring probes search all receivable signals of the base stations after receiving the instructions, quantize the intensities of the received signals of the base stations, establish base station signal intensity data tables in which the signal intensities of the base stations are arranged according to the serial numbers of the base stations, and send the base station signal intensity data tables to the data management center via the base station of which the received signal intensity is the largest; and
    C) operations are carried out based on each received current base station signal intensity data table sent by the corresponding wireless fetal monitoring probe and reference point base station signal intensity data tables which are obtained in advance and comprise base station signal intensities at a plurality of reference points in the set area to obtain a distance reference table expressing distance between the current position of the wireless fetal monitoring probe and each reference point; and the position of one reference point with the smallest distance value is selected to be regarded as the current position of the wireless fetal monitoring probe,
    wherein the method relates to a mobile terminal configured to download the current position of the wireless fetal monitoring probe from the data management center via the wireless base stations, and to display the current position of the wireless fetal monitoring probe; when finding out that the current wireless fetal monitoring probe disappears, a searching mode of the mobile terminal is started, and the mobile terminal emits electromagnetic waves the same as that of the wireless base stations, and displays response information of the wireless fetal monitoring probes, so as to search the wireless fetal monitoring probes.

2. The method for locating the wireless fetal monitoring probes in the set area of claim 1, further comprising the following steps before the step A:
    M) the wireless base stations are arranged at different positions in the set area; and
    N) the set area is divided into a plurality of locating sub-areas, and a reference point is arranged for each locating sub-area; the base station signal intensities at the reference points are acquired, and quantized to obtain the reference point base station signal intensity data tables; the reference point base station signal intensity data tables are saved.

3. The method for locating the wireless fetal monitoring probes in the set area of claim 2, wherein quantizing in the step B or the step N comprises: the receivable signal intensity value of each wireless base station is regarded as the signal intensity value of the base station, while if no signal intensity value of a base station is receivable, zero is regarded as the signal intensity value of the base station; signal intensity values acquired by each wireless fetal monitoring probe or at a certain point are arranged according to the serial number sequence of the wireless base stations, so as to obtain the base station signal intensity data table or the reference point base station signal intensity data table at the point.

4. The method for locating the wireless fetal monitoring probes in the set area of claim 3, wherein in the reference point base station signal intensity data table, the signal levels of all of the receivable signals of the wireless base stations are required to be larger than a set signal level or signal intensity, otherwise, the requirement is met by moving corresponding wireless base station(s) or by increasing the number of the wireless base stations.

5. The method for locating the wireless fetal monitoring probes in the set area of claim 1, wherein the method further comprises the following steps:
D) the current positions of the wireless fetal monitoring probes are marked in a map drawn in advance.

6. The method for locating the wireless fetal monitoring probes in the set area of claim 1, wherein the method further comprises the following steps:
the data management center sends probe sounding instructions with identification numbers of the wireless fetal monitoring probes to enable buzzers on the wireless fetal monitoring probes matched with the identification numbers to sound after the wireless fetal monitoring probes receive the instructions.

7. The method for locating the wireless fetal monitoring probes in the set area of claim 1, wherein the method further comprises the following steps:
when a wireless fetal monitoring probe(s) cannot receive any signal of the wireless base stations, physiological data obtained by the wireless fetal monitoring probe(s), current state data of the wireless fetal monitoring probe(s) and time data are saved in the wireless fetal monitoring probe(s), and are sent to the data management center as long as the wireless fetal monitoring probe(s) can receive a signal(s) of the wireless base stations.

8. The method for locating the wireless fetal monitoring probes in the set area of claim 1, wherein the data management center sends instructions to search the wireless fetal monitoring probes or exchange data with the wireless fetal monitoring probes via the wireless base stations connected with the data management center or wireless base stations of the data management center.

9. A system for implementing the method for locating the wireless fetal monitoring probes in the set area of claim 1, comprising:
a data management center, a plurality of wireless base stations and the wireless fetal monitoring probes,
wherein the data management center sends instructions via the wireless base stations arranged at different positions in the set area, so as to require the wireless fetal monitoring probes in the action scopes of the wireless base stations to send base station signal intensity data tables of received base station signals,
wherein each wireless fetal monitoring probe searches receivable signals of the base stations after receiving the instructions, quantizes the intensities of the received signals of the base stations, establishes a base station signal intensity data table in which signal intensities of the base stations are arranged according to the serial numbers of the base stations, and sends the base station signal intensity data table to the data management center via the base station of which the signal intensity is the largest;
wherein the data management center carries out operations based on each received current base station signal intensity data table sent by the corresponding wireless fetal monitoring probe and reference point base station signal intensity data tables which are obtained in advance and comprise the base station signal intensities at a plurality of reference points in the set area to obtain a distance reference table of distance values between the wireless fetal monitoring probe and the reference points, wherein the position of a reference point with the smallest distance value is selected to be regarded as the current position of the wireless fetal monitoring probe,
wherein the data managing center relates to a mobile terminal configured to download the current position of the wireless fetal monitoring probe from the data management center via the wireless base stations, and to display the current position of the wireless fetal monitoring probe; when finding out that the current wireless fetal monitoring probe disappears, a searching mode of the mobile terminal is started, and the mobile terminal emits electromagnetic waves the same as that of the wireless base stations, and displays response information of the wireless fetal monitoring probes, so as to search the wireless fetal monitoring probes.

10. The system of claim 9, wherein the data management center divides the set area into a plurality of locating sub-areas, collects the base station signal intensities at the reference points, and quantizes the base station signal intensities to obtain the reference point base station signal intensity data tables, and to save the reference point base station signal intensity data tables, wherein a reference point is arranged for each locating sub-area.

11. The system of claim 9, wherein each of the wireless fetal monitoring probes saves physiological data, current state data and time data when the wireless fetal monitoring probe(s) cannot receive any signal of the wireless base stations, and sends the saved data to the data management center as long as the wireless fetal monitoring probe(s) receives a signal(s) of the wireless base stations; wherein the data management center marks the current positions of the wireless fetal monitoring probes in a map drawn in advance.

* * * * *